United States Patent [19]

Hogan

[11] Patent Number: 4,935,011

[45] Date of Patent: Jun. 19, 1990

[54] SHEATH FOR INTRAVENOUS NEEDLE

[75] Inventor: J. Martin Hogan, Long Beach, Calif.

[73] Assignee: City of Hope, Duarte, Calif.

[21] Appl. No.: 221,875

[22] Filed: Jul. 20, 1988

Related U.S. Application Data

[63] Continuation-in-part of Ser. No. 102,428, Sep. 29, 1987, Pat. No. 4,820,282.

[51] Int. Cl.$^5$ ............................................. A61M 5/00
[52] U.S. Cl. ..................................... 604/177; 604/162; 604/198; 604/263
[58] Field of Search ............... 206/364, 365; 604/162, 604/164–169, 177–180, 192, 198, 263

[56] References Cited

U.S. PATENT DOCUMENTS

| | | | |
|---|---|---|---|
| 2,854,976 | 8/1957 | Heydrich | 604/263 |
| 2,990,059 | 6/1961 | Hitt | 206/63.2 |
| 3,658,061 | 4/1972 | Hall | 604/263 |
| 3,709,223 | 1/1973 | Macalalad et al. | 604/262 |
| 3,901,226 | 8/1975 | Scardenzan | 604/180 |
| 3,973,565 | 8/1976 | Steer | 604/177 |
| 4,007,740 | 2/1977 | Owen | 604/263 |
| 4,129,128 | 12/1978 | McFarlane | 604/180 |
| 4,170,993 | 10/1979 | Alvarez | 604/198 X |
| 4,324,237 | 4/1982 | Buttaravoli | 604/180 |
| 4,659,330 | 4/1987 | Nelson et al. | 604/192 |
| 4,676,783 | 6/1987 | Jagger et al. | 604/177 |
| 4,737,144 | 4/1988 | Choksi | 604/198 |

Primary Examiner—Dalton L. Truluck
Attorney, Agent, or Firm—Edward S. Irons

[57] ABSTRACT

A multi-panel shield or sheath constructed to define an envelope into which an intravenous needle having a sharpened cannula may be withdrawn upon removal from a vein. The envelope has a compression flap adapted to overlie the venipuncture site while the needle is being withdrawn from the vein, whereby a nurse, doctor or other person using the device may exert pressure on the venipuncture site as the needle is being withdrawn. A gripping panel is also provided to facilitate holding of the sheath as the needle is being retracted into the envelope. After the needle has been withdrawn into the shield envelope, the panels may be folded over one another to completely enclose the needle for subsequent handling and/or disposal. In some embodiments of the inventions a non-folding sheath defining an envelope is utilized. Other embodiments have no compression panel.

17 Claims, 6 Drawing Sheets

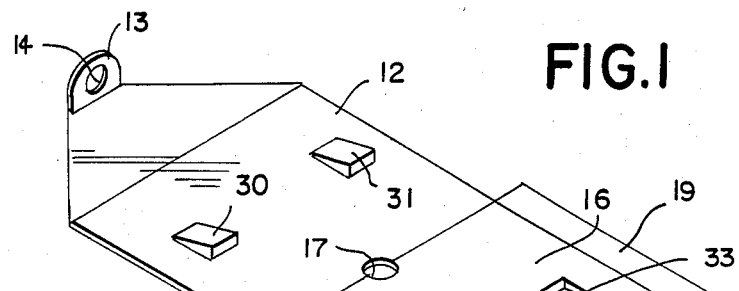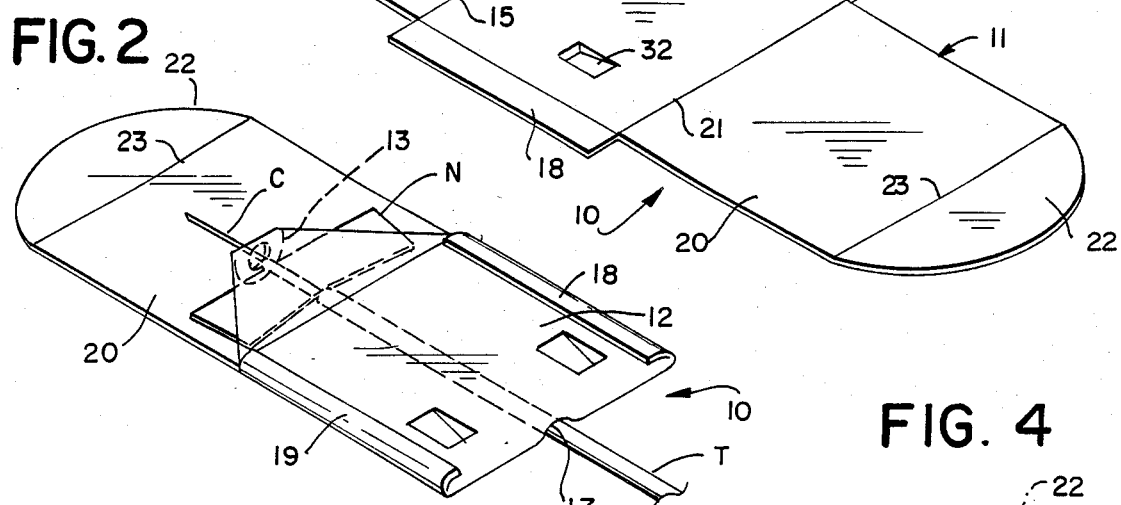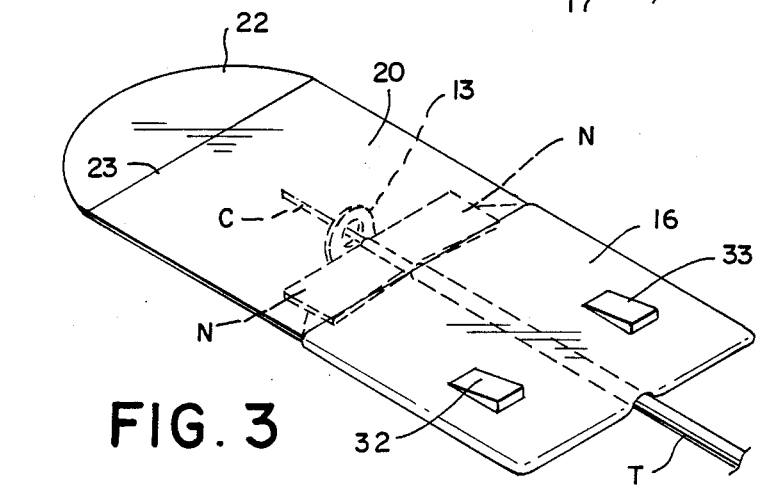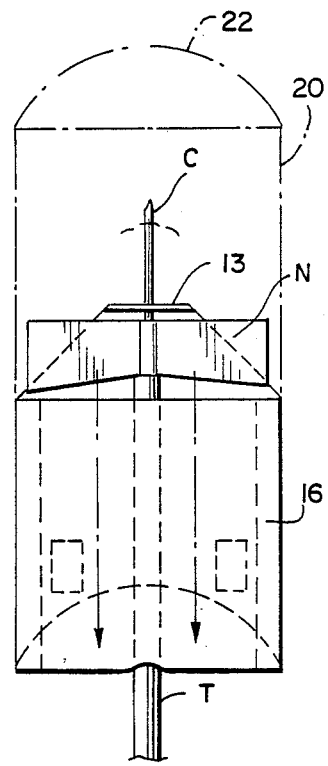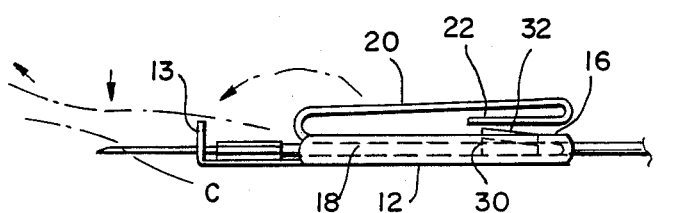

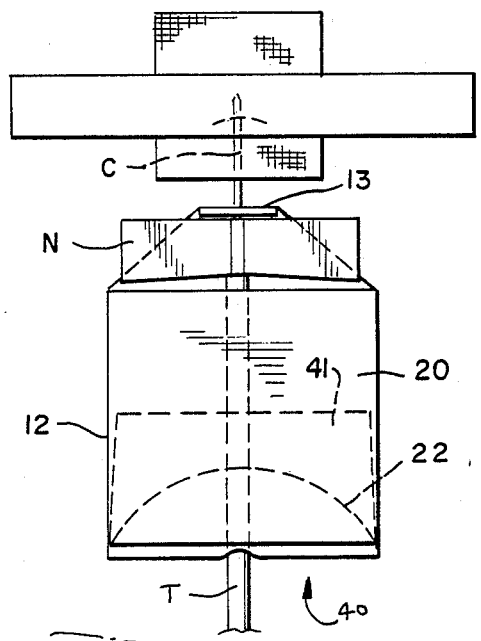
FIG. 11
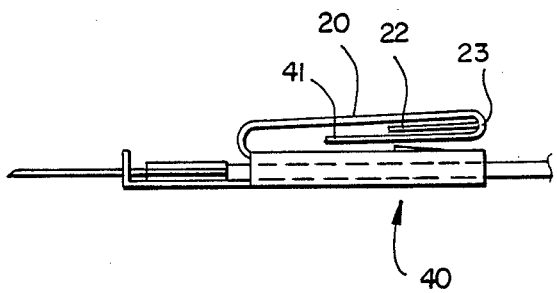
FIG. 12
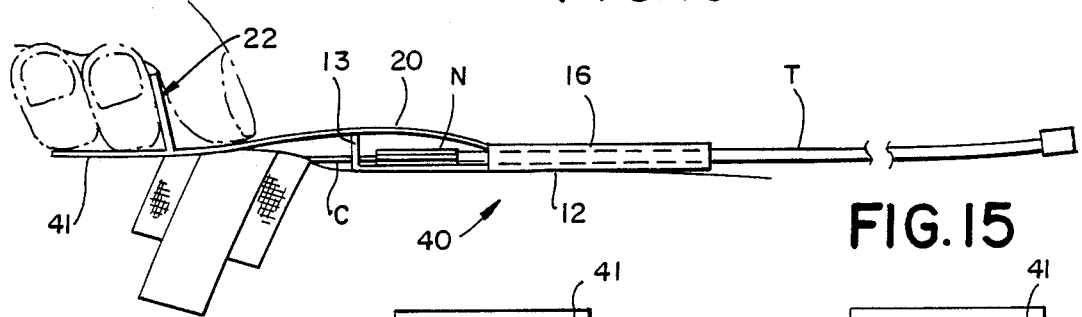
FIG. 13
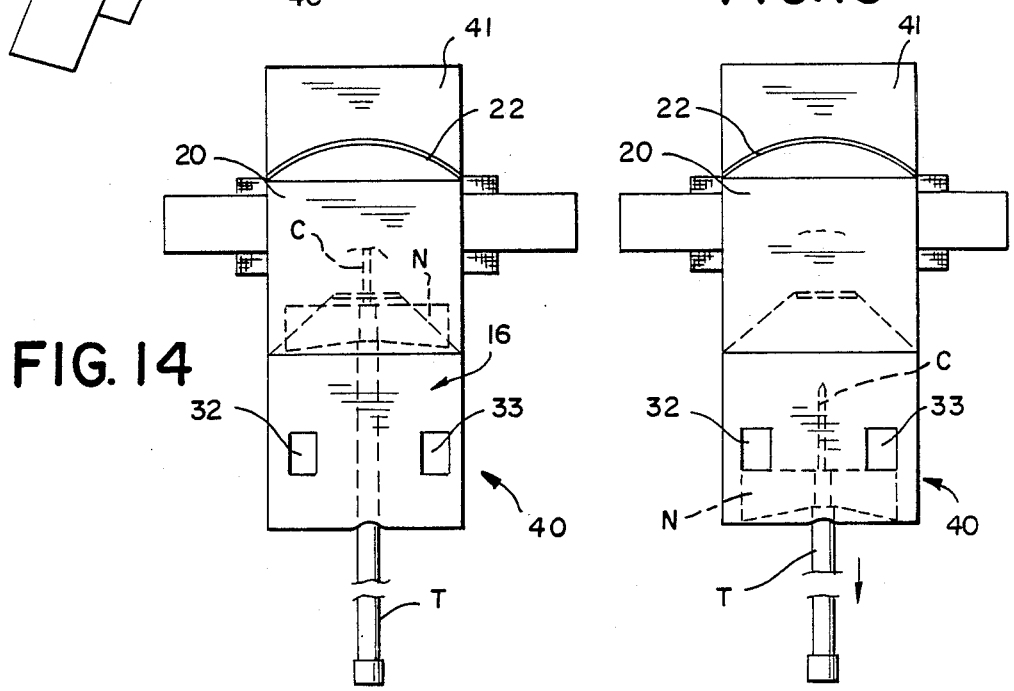
FIG. 14
FIG. 15

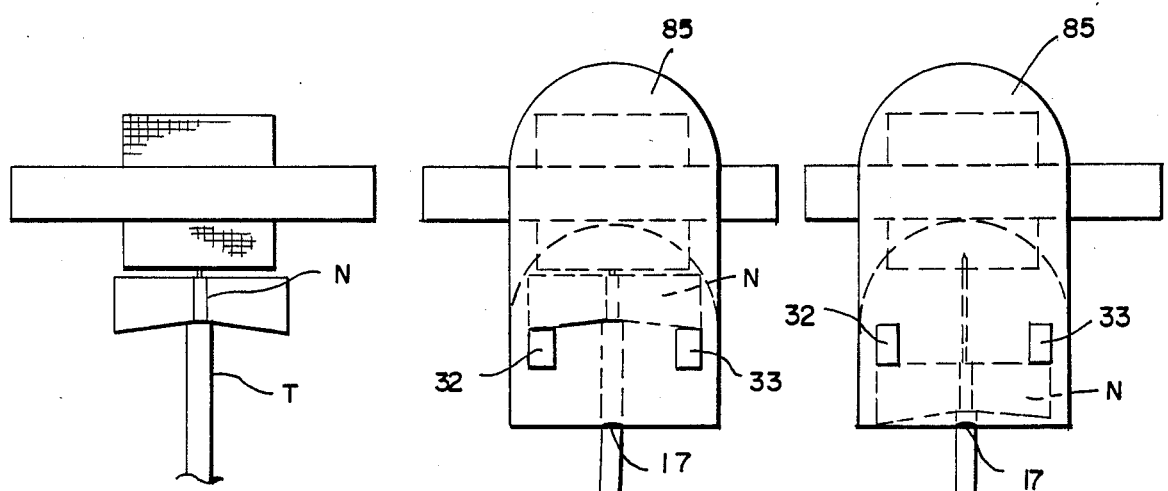
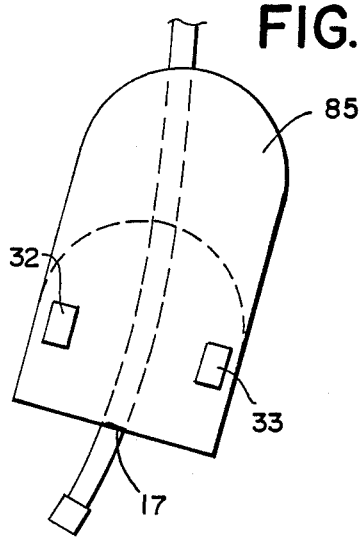
FIG. 26
FIG. 27
FIG. 28
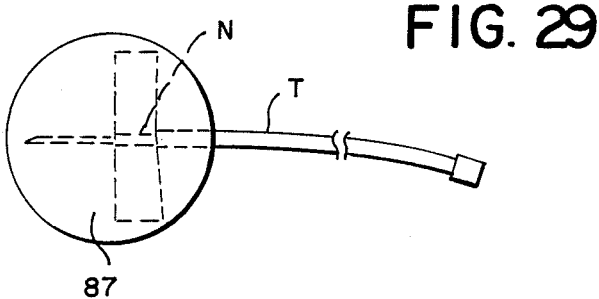
FIG. 29
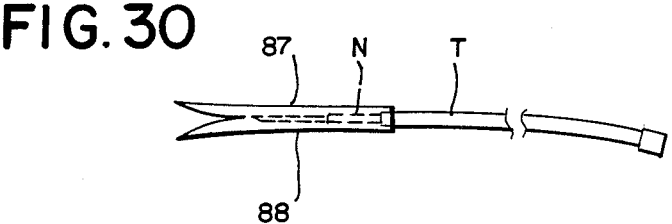
FIG. 30

SHEATH FOR INTRAVENOUS NEEDLE

This application is a continuation-in-part of application Ser. No. 102,428 filed Sept. 29, 1987, now U.S. Pat. No. 4,820,282 issued Apr. 11, 1989.

FIELD OF THE INVENTION

This invention relates to intravenous needles, and more particularly, to protective sheaths therefor.

BACKGROUND OF THE INVENTION

The danger of disease transmission among personnel who come into contact with contaminated materials or diseased persons, and especially the danger to those exposed to blood or other body fluids, has motivated the development of various devices and methods to prevent inadvertent infection.

It is especially desirable to provide means for protection from accidental pricking or puncture with contaminated intravenous needles. The problem is particularly acute in the collection and handling of blood or other body fluids when needles are used to pierce a vein and/or to transfer such fluids to various receptacles for testing and the like. Such means should be inexpensive, easy to use and provide for easy manipulation of the needle into and out of operative shielded and unshielded relationship.

In response to this problem, various shield devices have been developed to limit the exposure of personnel to the sharp point of the needle. Examples of prior art shields are shown in U.S. Pat. Nos. 4,659,330 and 4,737,114. Each of these patents describes tubular sheaths which encase the needle when the needle is not in use. Other needle protecting devices are disclosed in U.S. Pat. Nos. 2,854,976, 2,990,059, 3,709,223, 3,901,226, 3,973,565, 4,007,740 and 4,170,993. These patents do not suggest a shield envelope into which the needle may be withdrawn as it is removed from the venipuncture site.

SUMMARY OF THE INVENTION

It is an object of this invention to provide a shield or protective sheath for an intravenous needle to protect health workers from needle pricks and inadvertent contact with contaminated needles.

A further object of the invention is to provide a sheath that is slidable along associated tubing into covering relationship with a needle during and after retraction from a vein or the like.

Another object is to provide an intravenous needle sheath that includes foldable panels which may be quickly and easily placed into and out of shielding relationship with the needle.

The invention also provides a needle sheath that includes overlying shielded portions and portions defining gripping means for manipulating the sheath and needle.

Another object of the invention is to provide a needle sheath that includes foldable panels positioned to cover or shield the venipuncture site while the needle is in place and also during and after retraction into the sheath.

These objects are accomplished in some embodiments of the invention by a novel multipanel shield or sheath which is folded to define an envelope into which the needle may be withdrawn after use, and which has a flap adapted to overlie the venipuncture site while the needle is being withdrawn from a vein. This flap may also serve as a compression plate through which a nurse, doctor or other person using the device may exert pressure on the venipuncture site as the needle is being withdrawn. A gripping panel is also provided to facilitate holding of the sheath as the needle is being retracted into the envelope. After the needle has been withdrawn into the shield envelope, the panels may be folded over one another to completely enclose the needle for subsequent handling and/or disposal.

Other embodiments of the invention provide needle sheaths with a non-folding compression panel and with no compression panel.

BRIEF DESCRIPTION OF THE DRAWINGS

The foregoing and other objects and advantages of the invention will become apparent from the following detailed description and accompanying drawings, wherein like reference characters designate like parts throughout the several views, and wherein:

FIG. 1 is a top perspective view of the blank used to make a first form of sheath in accordance with the invention, showing the sheath in unfolded conditions.

FIG. 2 is a bottom perspective view of the sheath of FIG. 1, showing the sheath folded to define an envelope and with an intravenous needle in place for insertion into the vein of a patient and with the compression flap and gripping panel extended over the needle.

FIG. 3 is a top perspective view of the sheath of FIG. 2.

FIG. 4 is a top plan view of the sheath and needle combination of FIGS. 2 and 3, showing the sheath and needle in position for insertion into the vein of a patient.

FIG. 5 is a side view in elevation of the sheath and needle combination of FIG. 4.

FIG. 11 is a top plan view of the first modification, in which a flap extension is provided beyond the point of attachment of the gripping panel.

FIG. 12 is a side view of the sheath of FIG. 11.

FIG. 13 is a schematic side view of the sheath of FIGS. 11 and 12, showing the manner of use of the sheath.

FIG. 14 is a top plan view of the sheath and needle combination of FIGS. 11-13, showing the needle inserted into a vein and the flap extension projecting beyond the venipuncture site.

FIG. 15 is a view similar to FIG. 14, but showing the needle retracted into the shield envelope.

FIGS. 26, 27 and 28 illustrate the manner of use of the device shown in FIGS. 23-25.

FIG. 29 is a sectional view of another modification of the invention which does not include a compression plate.

FIG. 30 is a top plan view of the device as shown in FIG. 29.

DETAILED DESCRIPTION OF THE PREFERRED EMBODIMENTS

Figure 6:
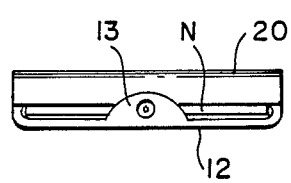
FIG. 6 is a front view of the sheath and needle combination of FIG. 5.
Figure 7:
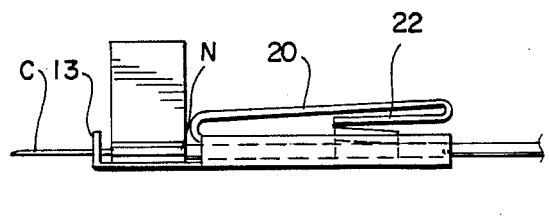
FIG. 7 is a side view similar to FIG. 5, but with the wings on the needle or cannula set in an erect position.
Figure 8:
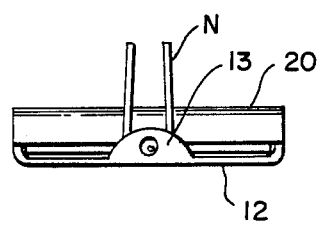
FIG. 8 is a similar view to FIG. 6 with the wings folded up.
Figure 10:
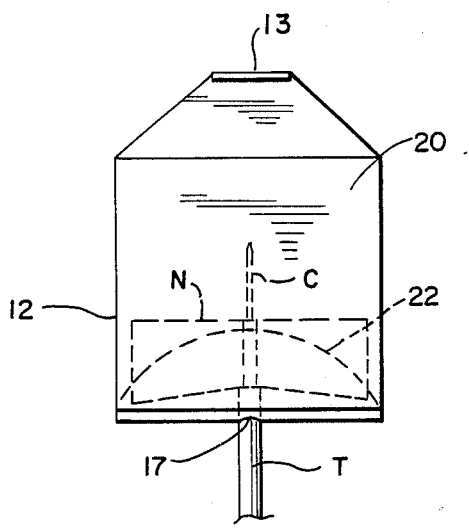
FIG. 10 is a top plan view of the sheath and needle combination of FIGS. 2-8, showing the needle retracted into the shield envelope.
Figure 9:
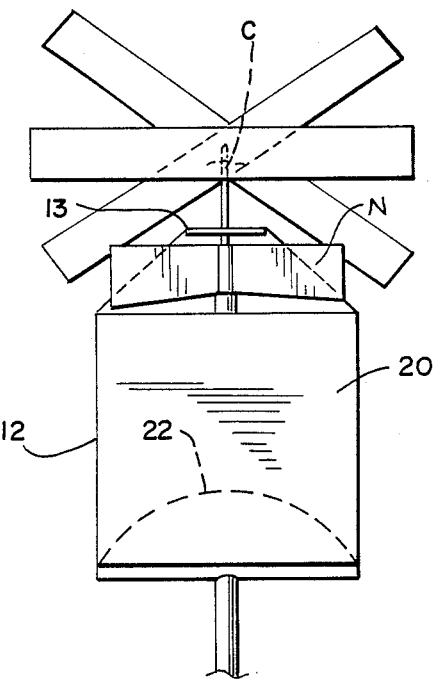
FIG. 9 is a top plan view of the sheath and needle combination of FIGS. 2-8, showing the needle inserted into the vein of a patient.

Referring more specifically to the drawings, a first form of shield or sheath in accordance with the invention is indicated generally at 10 in FIGS. 1–10. In FIG. 1, the unfolded blank 11 for the sheath of the invention is shown in perspective view and comprises a base plate 12 over which a winged or butterfly needle "N" lies when in use. A cannula retention tab 13 is formed on the free end of the base plate 12 and has an opening 14 therethrough for receiving the sharpened cannula "C" of needle "N". The other end of the base plate is joined at a fold line 15 with a top plate 16 which is adapted to overlie the needle when in use. An opening 17 is formed through the shield at the fold line for receiving the tubing "T" leading to Needle "N". A pair of side tabs 18 and 19 extend along the sides of top plate 16 and are folded and secured over the adjacent edges of the base plate when the top plate and base plate are folded into overlying relationship with one another about fold line 15, as shown best in FIG. 2. These side tabs maintain the top plate and base plate in folded relationship and define an envelope for receiving the needle (see FIGS. 2, 4 and 10).

A compression plate 20 is joined to the other end of the top plate 16 along fold line 21, and a gripping plate or tab 22 is joined at fold line 23 to the opposite end of the compression plate. Thus, when the panels are folded into operative relationship, the compression plate and gripping plate or tab project beyond the end of the needle as shown in FIGS. 2 and 3. Consequently, the sharpened end of the cannula is shielded to protect the user from accidental pricking or contact therewith. Further, after the needle has been inserted into a patient's vein, the compression plate may overlie the venipuncture site (see FIG. 3).

Additionally, the base plate has a pair of needle retention or locking ramps 30 and 31 formed therein, upstanding from the plane of the base plate. A pair of mating recesses 32 and 33 are formed in the top plate in position to receive the locking ramps when the base plate and top plate are folded over one another. Thus, when the cannula is withdrawn from the vein of the patient and the needle is retracted into the envelope, the wings of the needle ride over the ramps and engage behind them, retaining or locking the needle into shielded position within the envelope (see FIG. 10).

For inserting the cannula into the vein of a patient, the compression plate 20 and gripping tab 22 are folded about their respective fold lines to position the compression plate above the top plate, as shown in FIGS. 4–10, and the wings of the needle are bent upwardly to enable them to be gripped for insertion of the cannula into the vein. Tape, with or without a gauze pad, may then be placed over the venipuncture site and over at least portions of the wings of the needle to retain the cannula in place. The compression late and gripping tab may be left in their folded positions shown in FIGS. 4–10 until it is desired to remove the cannula from the vein. Then, the compression plate is extended over the venipuncture site so that the nurse, doctor or other person removing the cannula may apply pressure to the venipuncture site while the cannula is withdrawn from the vein by pulling the tubing back to retract the needle into the envelope. During this time, the gripping tab is grasped to retain the shield in position and to enable the needle to be retracted into the envelope and past the locking ramps. Accordingly, protection to the user from the sharpened point of the cannula is assured at all times. Moreover, the compression plate acts as a shield to prevent blood from spurting onto the user as the cannula is being withdrawn.

A first modification to the invention is indicated generally at 40 in FIGS. 11–15. In this form of the invention, an extension panel 41 is joined to the end of compression plate 20 at fold line 23, whereby the gripping tab 22 is positioned such that even further protection is afforded to the user as the cannula is being withdrawn from the vein (see FIG. 13). During insertion of the cannula into the vein, the extension panel and gripping tab are folded under as shown in FIGS. 11 and 12. However, for withdrawal of the cannula from the vein, the compression plate 20, extension plate or panel 41 and gripping tab 22 are extended forwardly over the venipuncture site as shown in FIGS. 14 and 15. The extension panel, by extending beyond the venipuncture site, provides added protection to the user. Otherwise, use of this form of the invention is identical to that previously described.

Figure 16:
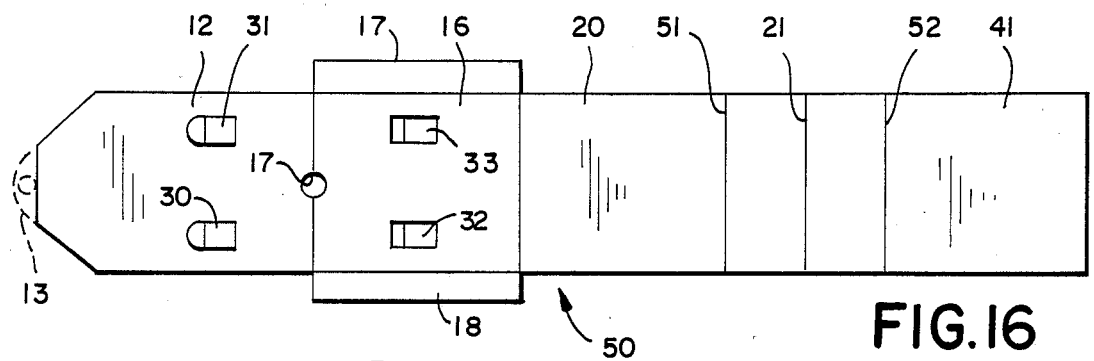
FIG. 16 is a plan view of the blank used in forming a second modification of the invention in which the gripping panel is defined by a pair of folded panels between the compression plate and the flap extension.
Figure 17:
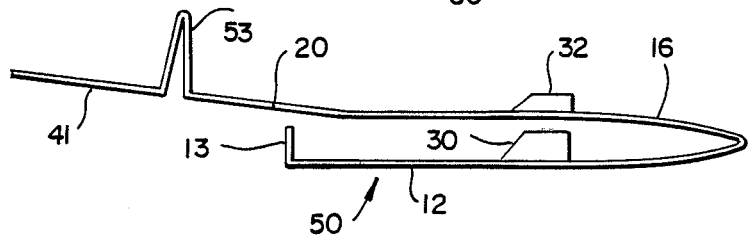
FIG. 17 is a side view of the second modification of the invention.
Figure 18:
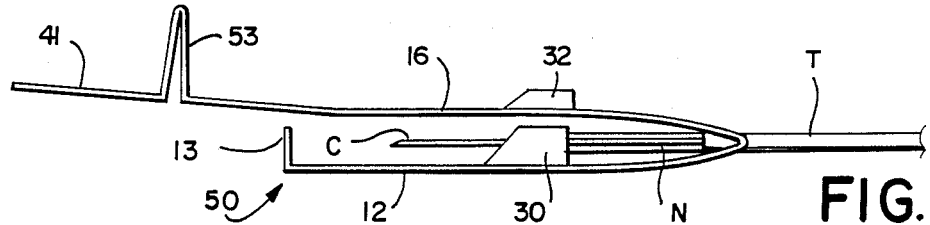
FIG. 18 is a side view of the sheath of FIG. 17, shown in partially folded condition and with a needle enclosed in the shield envelope.

A second modification to the invention is indicated generally at 50 in FIGS. 16–18. In this form of the invention, which is similar to that described immediately above, the gripping tab 22 is replaced with a further pair of fold lines 51 and 52 on opposite sides of the fold line 21 joining the compression plate 20 to the extension panel 41. Thus, by further folding the panels about the fold lines 51 and 52, a gripping tab 53 is formed at the juncture between the extension panel and the compression panel. This arrangement eliminates any difficulties which may be encountered in forming or attaching the earlier described gripping panel 22. In addition, as shown by dot-and-dash lines in FIG. 16, the cannula retention tab 13 and its function may be eliminated, if desired. This enables the shield to be moved along the length of tubing connected to the needle so that the shield may be moved out of the way when not needed, thereby providing room for use of a second needle. For example, a first needle aligned toward the wrist of a patient may be inserted into a vein, while a second needle aligned toward the elbow maybe inserted into a vein. In some instances when two needles are used as just described, use of a shield with the cannula retention tab results in interference between the two needles and their associated shields or sheaths.

Figure 19:
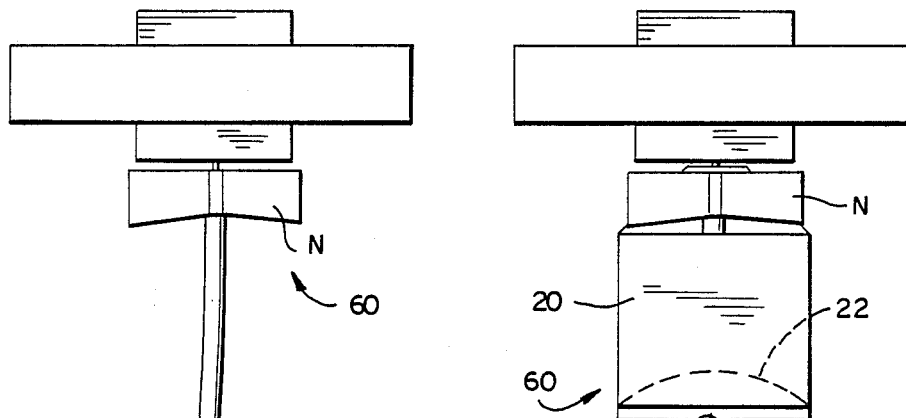
FIG. 19 is a top plan view of a third modification of the invention, in which the sheath is identical to that shown and described in relation to FIGS. 1–9, except that the cannula retention tab has been eliminated.
Figure 20:
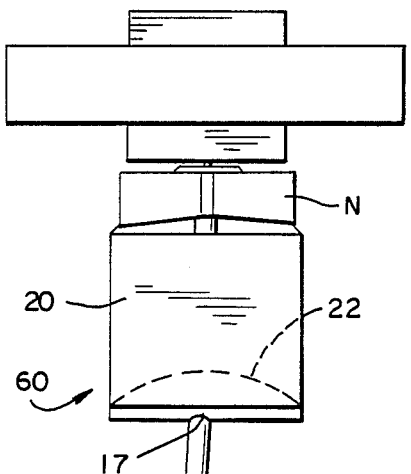
FIG. 20 is a top plan view of the sheath of FIG. 19, showing the sheath moved into position adjacent the needle.

A third modification to the invention is indicated generally at 60 in FIGS. 19 and 20. This form of the invention is identical to the first form of the invention described herein, except that the cannula retention tab 13 and its function are eliminated, resulting in the advantage described immediately above. Consequently, the needle may be positioned with the cannula inserted into a vein and secured as shown in FIG. 19, with the sheath slid along the tubing to an out-of-the-way position. When it is desired to remove the cannula from the vein, the sheath is slid along the tubing into contiguous relationship with the needle as shown in FIG. 20 and used as described before.

Figure 21:
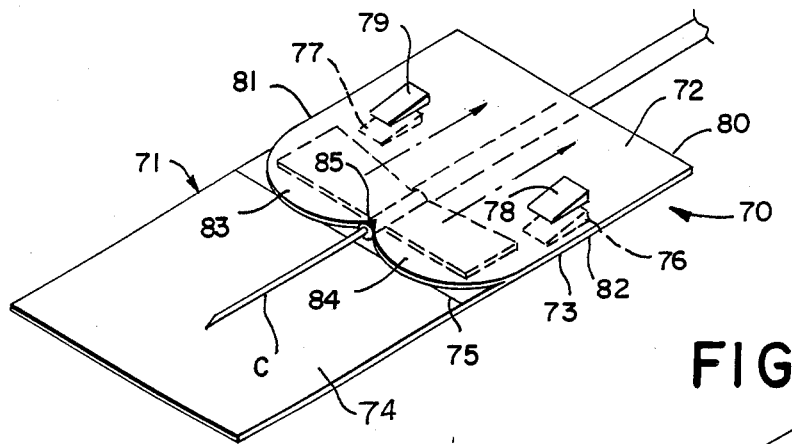
FIG. 21 is a top plan view of a fourth modification of the invention, in which guide tabs are formed on the bottom plate.
Figure 22:
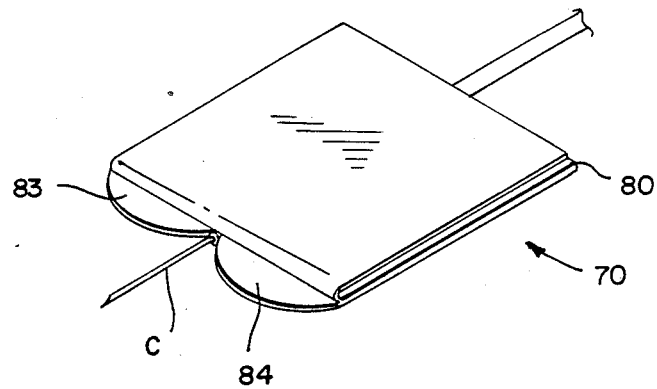
FIG. 22 is a top plan view of the sheath of FIG. 21, showing a needle in operative position in the sheath.
Figure 23:
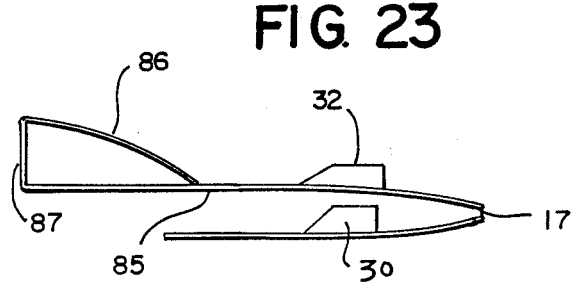
FIG. 23 is a side view of a further modification of the invention in which the compression panel and upper plate are a single non-folded element.
Figure 24:
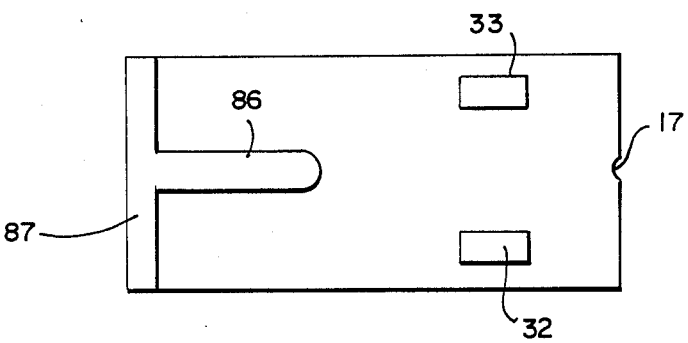
FIG. 24 is a top plan view of the embodiment of the invention shown in FIG. 23.
Figure 25:
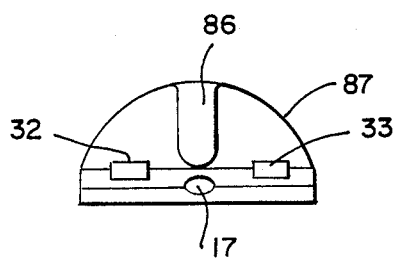
FIG. 25 is a rear perspective view of the invention shown in FIG. 23.

A fourth modification to the invention is indicated generally at 70 in FIGS. 21 and 22. In this form of the invention, the sheath 71 includes three panels, i.e., a base plate 72, top plate 73 and a compression panel 74 joined along a fold line 75 to the forward edge of the top plate. A pair of upstanding needle retention tabs 76 and 77 in the base plate and cooperating recesses 78 and 79 in the top plate retain the needle in the sheath after it is retracted into the shield envelope as previously described. The top plate and base plate may be formed as a single sheet joined along a fold line 80 at the rearward ends thereof, as in the previously described forms of the invention, and subsequently sealed to one another along adjacent side edges 81 and 82 to form the envelope. The base plate is formed with forwardly projecting guide tabs 83 and 84, defining a notch or recessed area 85 which is aligned with the needle to facilitate guiding of the needle during its insertion into a vein. The compression panel maybe extended to overlie the venipuncture site during withdrawal of the cannula, as shown in FIG. 21, or folded back over the top plate during insertion and use of the needle, as shown in FIG. 22.

The sheath may be made from any suitable material, such as molded synthetic plastic, metal, paper composition, etc. If made from molded plastic or paper materials, the side tabs 18 and 19 may be sealed to the top plate with an adhesive or heat seal or other suitable means, as desired or appropriate. Alternatively matching side tabs may be added to the top plate and sealed to the opposing side tabs without folding.

FIGS. 23-28 depict a fifth embodiment of the invention 70 in which the compression panel and upper plate are a single non-folded element 85. In this embodiment the compression panel is permanently extended. The element 85 may be provided with gripping surfaces or panels 86 and 87.

The manner of use of the device is apparent from FIGS. 26-28. Referring to the Figures, the device is initially spaced on the tube away from the needle "N". The device is then moved upwards along the tube to encase the needle in the envelope. The tube is then grasped and pulled rearwardly to move the needle "N" past the locking ridges upon removal from the vein or the like.

A sixth embodiment of the invention is shown in FIGS. 29 and 30. As there depicted, the invention comprises a pair of front and back convex shaped panels 87 and 88 which may be made of plastic material. The convex portion of the device provides resistance for the movement of the needle backwards and forwards within the device. The manner of use is similar to that described with respect to the embodiment shown in FIGS. 23-28. This embodiment may also be provided with locking ridges in which case the panels may be essentially parallel.

Although the invention has been described with reference to a particular embodiment, it is to be understood that this embodiment is merely illustrative of the application of the principles of the invention. Numerous modifications may be made therein and other arrangements may be devised without departing from the spirit and scope of the invention.

I claim:

1. An intravenous needle or the like connected to tubing and having a winged or butterfly body and a sharpened cannula
   a protective sheath slidably mounted on said tubing, said sheath comprising:
   a plurality of panels folded over one another to define an envelope, including a base plate adapted to lie under a needle and a top panel adapted to overlie the needle, said panels having an opening at a forward end portion thereof for extension therethrough of said sharpened cannula.

2. A protective sheath as claimed in claim 1, wherein: said foldable panels have an opening through a rearward end portion thereof for receiving tubing connected to the needle, said sheath being slidable along said tubing whereby the needle and tubing may be moved axially relative to the sheath to enable the cannula to be extended through the forward opening and to enable the needle to be retracted into the envelope defined by the top panel and base plate with the sharpened point of the cannula positioned within and shielded by the envelope.

3. A protective sheath as claimed in claim 2, wherein: at least one of said top panel and bottom plate have needle retention means thereon for retaining said needle in its retracted position in the envelope.

4. A protective sheath as claimed in claim 3, wherein: the retention means comprises a raised projection or ramp on opposite sides of the base plate configured to enable the wings of the needle to ride rearwardly thereover but prevent reverse, forward movement of the wings over the projections.

5. A protective sheath as claimed in claim 4, wherein: the opposite side edges of said top panel and base plate are secured to one another.

6. A protective sheath as claimed in claim 5, wherein: said sheath is made of molded synthetic plastic,. material.

7. A protective sheath as claimed in claim 5, wherein: said sheath is made of paper composition.

8. A protective sheath as claimed in claim 1, wherein: a cannula retention tab is formed on the end of the base plate, said retention tab having an opening therethrough for receiving the cannula to maintain the cannula in alignment and in operative relationship with the sheath.

9. A protective sheath for intravenous needles and the like having a winged or butterfly-type body and a sharpened cannula, comprising:
   a plurality of panels folded over one another to define an envelope, including a base plate adapted to lie under a needle and a top panel adapted to overlie the needle, said panels having an opening at a forward end portion thereof for extension therethrough of said sharpened cannula;

and an opening through a rearward end portion thereof for receiving tubing connected to the needle, said sheath being slidable along said tubing whereby the needle and tubing may be moved axially relative to the sheath to enable the cannula to be extended through the forward opening and to enable the needle to be retracted into the envelope defined by the top panel and base plate with the sharpened point of the cannula positioned within and shielded by the envelope; and a foldable compression panel joined along a fold line to a forward end portion of said top panel, and adapted to be extended over a venipuncture site during withdrawal of the cannula from a vein so that a person using the needle may exert compression on the venipuncture site while being protected from the sharpened point of the cannula.

10. A protective sheath as claimed in claim 9, wherein:

a gripping tab is formed on the forward end of said compression panel to enable the sheath to be held in position while the needle is being retracted into the envelope.

11. A protective sheath as claimed in claim 10, wherein:

an extension flap projects forwardly from the end of the compression panel to extend beyond and shield the venipuncture site when the compression panel is extended to overlie the venipuncture site, thereby shielding the user from the sharpened point of the cannula as it is being withdrawn from a vein.

12. A protective sheath as claimed in claim 11, wherein:

the gripping tab and extension flap are joined along a common fold line to the forward end of the compression panel.

13. A protective sheath as claimed in claim 11, wherein:

the extension flap is joined to the forward end of the compression panel via a pair of relatively narrow panels connected to each other and to the extension flap and compression panel, respectively, along three parallel, spaced apart fold lines, whereby the two narrow panels may be folded against one another to form the gripping panel.

14. A protective sheath as claimed in claim 12, wherein:

a cannula retention tab is formed on the end of the base plate, said retention tab having an opening therethrough for receiving the cannula to maintain the cannula in alignment and in operative relationship with the sheath, said cannula retention tab also extending the base plate sufficiently forward to allow the cannula wings to be folded upward without interference from the top panel.

15. A protective sheath as claimed in claim 13, wherein:

a cannula retention tab is formed on the end of the base plate, said retention tab having an opening therethrough for receiving the cannula to maintain the cannula in alignment and in operative relationship with the sheath.

16. A protective sheath for an intravenous needle having a sharpened cannula and a winged or butterfly type body attached to a length of tubing said sheath comprising:

an envelope including a base panel adapted to lie under a needle and a top panel adapted to overlie the needle, said envelope having an opening at a forward and rearward portion thereof through which said tubing may be passed, the opening at said forward portion of said envelope being adapted for extension of said cannula therethrough, said sheath being slidable along said tubing, whereby the needle and tubing may be moved axially relative to the sheath to enable the cannula to be extended through the forward opening for insertion of the cannula into a vein, and to enable the needle to be retracted into the envelope defined by the top panel and bottom panel with the sharpened point of the cannula positioned within and shielded by the envelope.

17. A needle having a distal end for insertion into a patent and a proximal end connected to a tube;

butterfly shaped side strips attached adjacent the proximal end of said needle; and sheath means including foldable panels and being slidably mounted on said tube for movement into a covering relationship with said needle while said needle is inserted and during and after retraction of said needle.

* * * * *

UNITED STATES PATENT AND TRADEMARK OFFICE
CERTIFICATE OF CORRECTION

PATENT NO. : 4,935,011
DATED : June 19, 1990
INVENTOR(S) : J. Martin Hogan

It is certified that error appears in the above-identified patent and that said Letters Patent is hereby corrected as shown below:

Column 8, line 39, delete "patent" and insert --patient--.

Signed and Sealed this

Ninth Day of March, 1993

Attest:

STEPHEN G. KUNIN

*Attesting Officer*   Acting Commissioner of Patents and Trademarks